United States Patent
Bitan et al.

(10) Patent No.: US 10,718,618 B2
(45) Date of Patent: Jul. 21, 2020

(54) AUTOMATICALLY CREATING A TERRAIN MAPPING DATABASE

(71) Applicant: Trailze, Ltd., Modiin (IL)

(72) Inventors: Ronen Bitan, Modiin (IL); Tal Lavi, Rechovot (IL)

(73) Assignee: Trailze, Ltd, Tel Aviv (IL)

( * ) Notice: Subject to any disclaimer, the term of this patent is extended or adjusted under 35 U.S.C. 154(b) by 113 days.

(21) Appl. No.: 15/698,279

(22) Filed: Sep. 7, 2017

(65) Prior Publication Data

US 2018/0058858 A1 Mar. 1, 2018

Related U.S. Application Data

(63) Continuation of application No. PCT/IB2016/051305, filed on Mar. 8, 2016.
(Continued)

(51) Int. Cl.
| | |
|---|---|
| *G01C 21/20* | (2006.01) |
| *G01C 21/10* | (2006.01) |
| *G01S 19/42* | (2010.01) |
| *G01V 99/00* | (2009.01) |
| *A61B 5/01* | (2006.01) |
| *A61B 5/021* | (2006.01) |
| *A61B 5/0404* | (2006.01) |
| *A61B 5/00* | (2006.01) |

(Continued)

(52) U.S. Cl.
CPC .............. *G01C 21/20* (2013.01); *A61B 5/01* (2013.01); *A61B 5/021* (2013.01); *A61B 5/0404* (2013.01); *A61B 5/6893* (2013.01); *G01C 21/10* (2013.01); *G01C 21/32* (2013.01); *G01C 21/3697* (2013.01); *G01S 19/42* (2013.01); *G01V 99/005* (2013.01); *G06F 16/29* (2019.01); *G09B 29/106* (2013.01)

(58) Field of Classification Search
CPC .... G01C 21/20; G01C 21/10; G01C 21/3697; G01C 21/32; G06F 16/29; G01S 19/42; A61B 5/01; A61B 5/0404; A61B 5/6893; A61B 5/021; G01V 99/005; G09B 29/106
USPC .......................................................... 701/450
See application file for complete search history.

(56) References Cited

U.S. PATENT DOCUMENTS

| | | | | |
|---|---|---|---|---|
| 2006/0155464 | A1* | 7/2006 | Smartt | G01C 21/32 701/450 |
| 2010/0332116 | A1 | 12/2010 | Sakashita | |
| 2014/0303892 | A1* | 10/2014 | Morlock | G01C 21/20 701/533 |

FOREIGN PATENT DOCUMENTS

| | | |
|---|---|---|
| EP | 2159777 A2 | 3/2010 |
| WO | 2008026949 A9 | 7/2009 |

OTHER PUBLICATIONS

The European Search Report and Supplementary Search Report for EP Application No. 16761178.9 dated Oct. 10, 2018, The Hague, EPO.

(Continued)

*Primary Examiner* — Brian P Sweeney
(74) *Attorney, Agent, or Firm* — M&B IP Analysts, LLC.

(57) ABSTRACT

A database for mapping off-road terrain of various characteristics in three-dimensional terms, comprising: a plurality of road segment entries, each containing data pertaining to the terrain characteristics of the segment; and a plurality of elbow entries, each containing (x, y, z) coordinates of the elbow and a record for each road segment having the elbow (Continued)

as one of its end points, the record comprising navigation directives for vehicles entering the segment from the elbow.

12 Claims, 8 Drawing Sheets

Related U.S. Application Data (60) Provisional application No. 62/131,314, filed on Mar. 11, 2015.

(51) Int. Cl.
*G06F 16/29* (2019.01)
*G01C 21/36* (2006.01)
*G01C 21/32* (2006.01)
*G09B 29/10* (2006.01)

(56) References Cited

OTHER PUBLICATIONS

A Notice of Deficiencies for EP Application No. 16761178.9 dated Aug. 22, 2019, EPO, Rijswijk, The Netherlands.

* cited by examiner

| SEGMENTS |||
|---|---|---|
| SEGMENT NO. | ELBOWS | CHARACTERISTICS |
| S200 | E210 | Dirt road |
| S210 | E210, E220 | Dirt road |
| S220 | E220, E230 | Gravel |
| S230 | E230, E240 | Gravel |
| S240 | E240, E250 | Dirt road |
| S250 | E250 | Dirt road |

Fig. 3A

| ELBOWS |||||
|---|---|---|---|
| ELBOW NO. | FROM SEGMENTS | TO SEGMENT | DIRECTIVES |
| E210 | S200 | S210 | |
| E220 | S210 | S220 | |
| E230 | S220 | S230 | |
| E240 | S230 | S240 | |
| E250 | S240 | S250 | |

| SEGMENTS |||
|---|---|---|
| SEGMENT NO. | ELBOWS | CHARACTERISTICS |
| S200 | E210 | Dirt road |
| S210 | E210, E220 | Dirt road |
| S520 | E220, E540 | Gravel |
| S530 | E540, E230 | Gravel |
| S230 | E230, E240 | Gravel |
| S240 | E240, E250 | Dirt road |
| S250 | E250 | Dirt road |

Fig. 6A

| ELBOWS | | | |
|---|---|---|---|
| ELBOW NO. | FROM SEGMENTS | TO SEGMENT | DIRECTIVES |
| E210 | S200 | S210 | |
| E220 | S210 | S520 | |
| E540 | S520 | S530 | |
| E230 | S530 | S230 | |
| E240 | S230 | S240 | |
| E250 | S240 | S250 | |

Fig. 6B

AUTOMATICALLY CREATING A TERRAIN MAPPING DATABASE

CROSS-REFERENCE TO RELATED PATENT APPLICATIONS

This application is a continuation of International Application No. PCT/IB2016/051305, filed Mar. 8, 2016. The International Application claims the benefit of U.S. Provisional Application No. 62/131,314, filed Mar. 11, 2015. Both applications are incorporated by reference in their entirety herein.

TECHNOLOGY FIELD

The present invention relates to navigation, specifically to creating and maintaining an updated database for presenting three-dimensional guidance information to a user traveling by vehicle or pedestrian.

SUMMARY

According to an aspect of the present invention, there is provided a database for mapping off-road terrain of various characteristics in three-dimensional terms, comprising: a plurality of road segment entries, each containing data pertaining to the terrain characteristics of the segment; and a plurality of elbow entries, each containing (x, y, z) coordinates of the elbow and a record for each road segment having the elbow as one of its end points, the record comprising navigation directives for vehicles entering the segment from the elbow.

Each one of the road segment entries further comprises pointers to elbow entries of its end points.

The navigation directives include consideration of the vehicle type.

The navigation directives include consideration of the road segment that led the vehicle to the elbow.

The navigation directives include 3 D considerations.

The navigation directives include consideration of user skills.

The terrain characteristics within each the segment are substantially homogenous and configured to be traversed using a single set of the directives.

The directives are configured to be defined according to indications selected from the group consisting of: mounting slope, descending slope, sharp turn, rocky terrain, bridge over river, gravel, mud and hiking section.

The indications are configured to be translated into the directives depending on the type of the vehicles.

The directives are stored in the database along with references to the appropriate type of the vehicle.

The terrain characteristics further comprise at least one of sand, gravel and rock.

The navigation directives for the road segments are configured to be continuously derived from various sensors, cameras and microphones carried or worn by a traveler.

The sensors are selected from the group consisting of: motion sensors, environmental sensors, position sensors and wearable physiological monitoring sensors.

The motion sensors are selected from the group consisting of: accelerometers, gravity sensors, gyroscopes and rotational vector sensors.

The environmental sensors are selected from the group consisting of: barometers, photometers and thermometers.

The position sensors are selected from the group consisting of: orientation sensors, magnetometers, Global Positioning System (GPS), European Geostationary Navigation Overlay Service (EGNOS) and Global Navigation Satellite System (GLONASS).

The wearable physiological monitoring sensors are configured to measure physiological parameters selected from the group consisting of: electrocardiogram (ECG), heart rate, blood pressure and body temperature.

According to another aspect of the present invention, there is provided a method of creating and continuously updating a database for mapping off-road terrain of various characteristics in three-dimensional terms, comprising: defining a plurality of road segment, each road segment defining two bounding elbows, using at least one of maps and recorded trails; for each road segment: defining preliminary terrain characteristics; for each elbow defined by the road segment: defining preliminary navigation directives for vehicles entering the segment from the elbow; and continuously updating the database using at least one of recorded trails and data from sensors carried or worn by travelers.

The updating comprises updating segment definitions according to recorded trails intersecting existing segments.

The updating comprises updating segment definitions according to sensors data indicating change in terrain characteristics within existing road segments.

The sensors are selected from the group consisting of: motion sensors, environmental sensors, position sensors and wearable physiological monitoring sensors.

BRIEF DESCRIPTION OF THE DRAWINGS

For better understanding of the invention and to show how the same may be carried into effect, reference will be made, purely by way of example, to the accompanying drawings.

With specific reference to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION OF PREFERRED EMBODIMENTS

The present invention provides a novel database for mapping terrain of various characteristics in three-dimensional terms. The database is constructed automatically in the system by analyzing previously recorded travelers' trails and current feedback from sensors, as will be explained in detail below.

Figure 1:
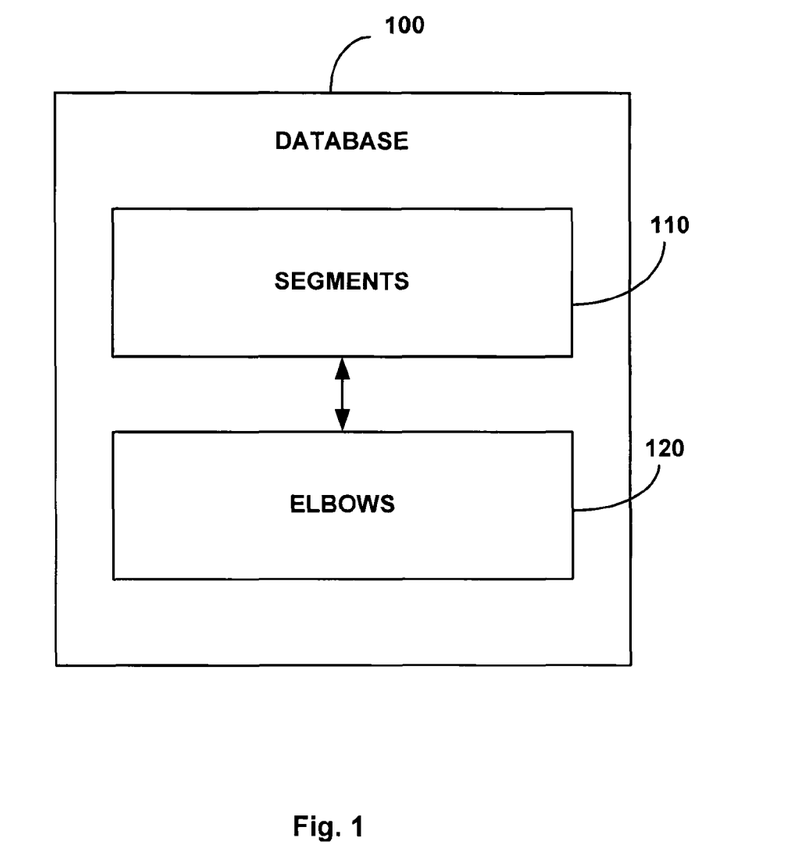
FIG. 1 is a schematic block diagram of the database according to the present invention.

FIG. 1 is a schematic block diagram of the database 100 according to the present invention, comprising road segments 110 and elbows 120.

Each road segment entry 110 contains data pertaining to the terrain characteristics of the segment. In a preferred embodiment of the invention the terrain characteristics within each segment are substantially homogeneous and may be traversed using a single set of directives. Each road segment entry may also optionally point to its two bounding elbows (end points). Terrain characteristics may be, for example, sand, gravel, rock, etc.

Each elbow entry 120 includes (x, y, z) coordinates of the elbow and a record for each road segment having the elbow as one of its end points, the record including navigation directives for vehicles (or pedestrians) entering the segment from the elbow.

The directives may take into consideration:

Type of vehicle if any (e.g. 4 WD, motorbike, mountain bike, horse, pedestrian etc.)

The road segment that led the vehicle/user to the elbow and specifically 3D considerations, namely altitude changes between the segments.

Various skill levels of users in any of the vehicle types.

Figure 2:
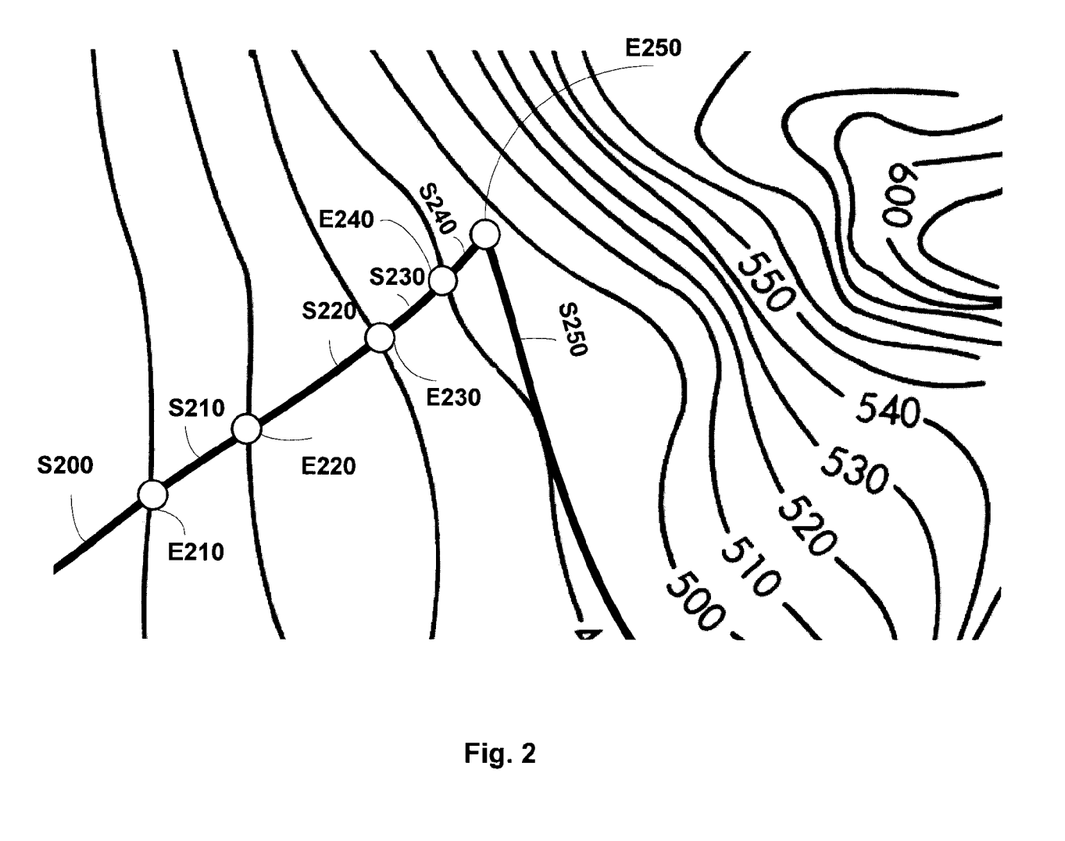
FIG. 2 is a schematic representation of a partial trails map.
Figure 3A:
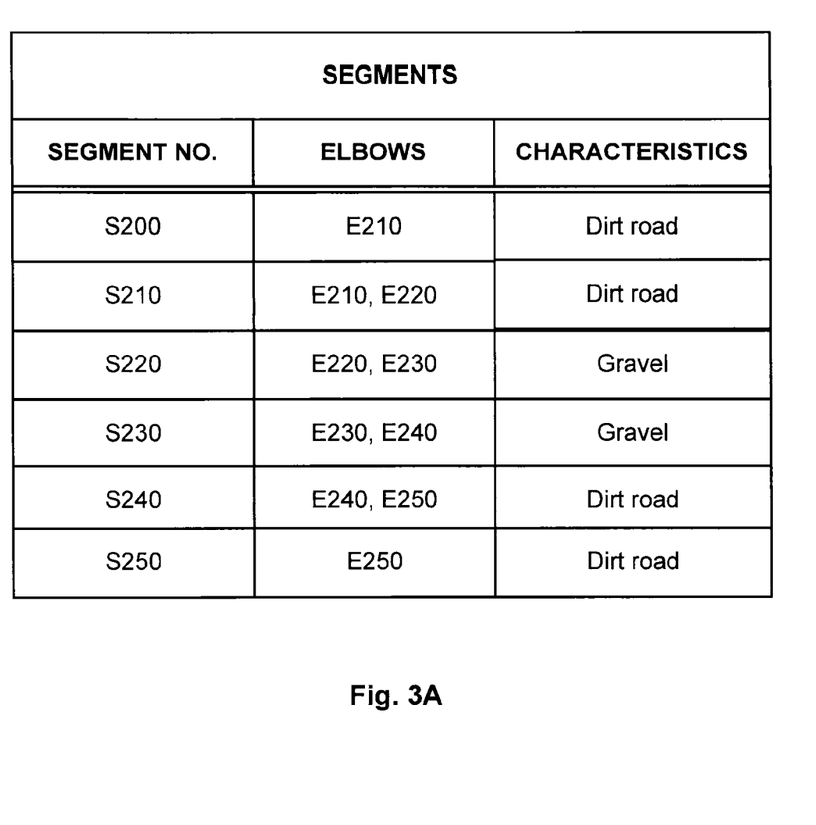
FIGS. 3A and 3B show exemplary database entries describing the partial trails of FIG. 2.
Figure 3B:
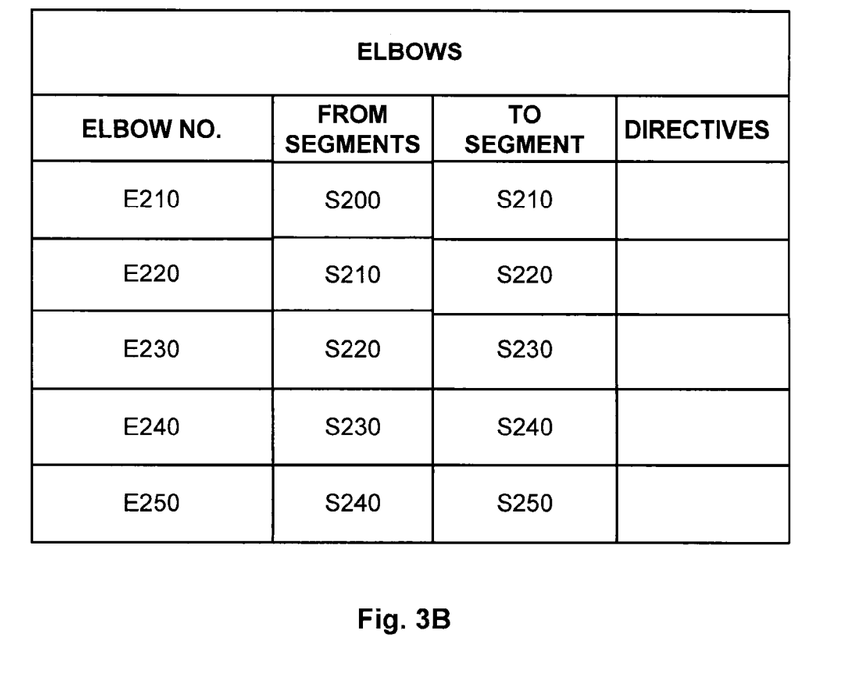

FIG. 2 is a schematic representation of a partial 3 D trails map described by the exemplary database entries in FIGS. 3A and 3B.

The database 100 is continuously updated, as will be explained below.

Figure 4:
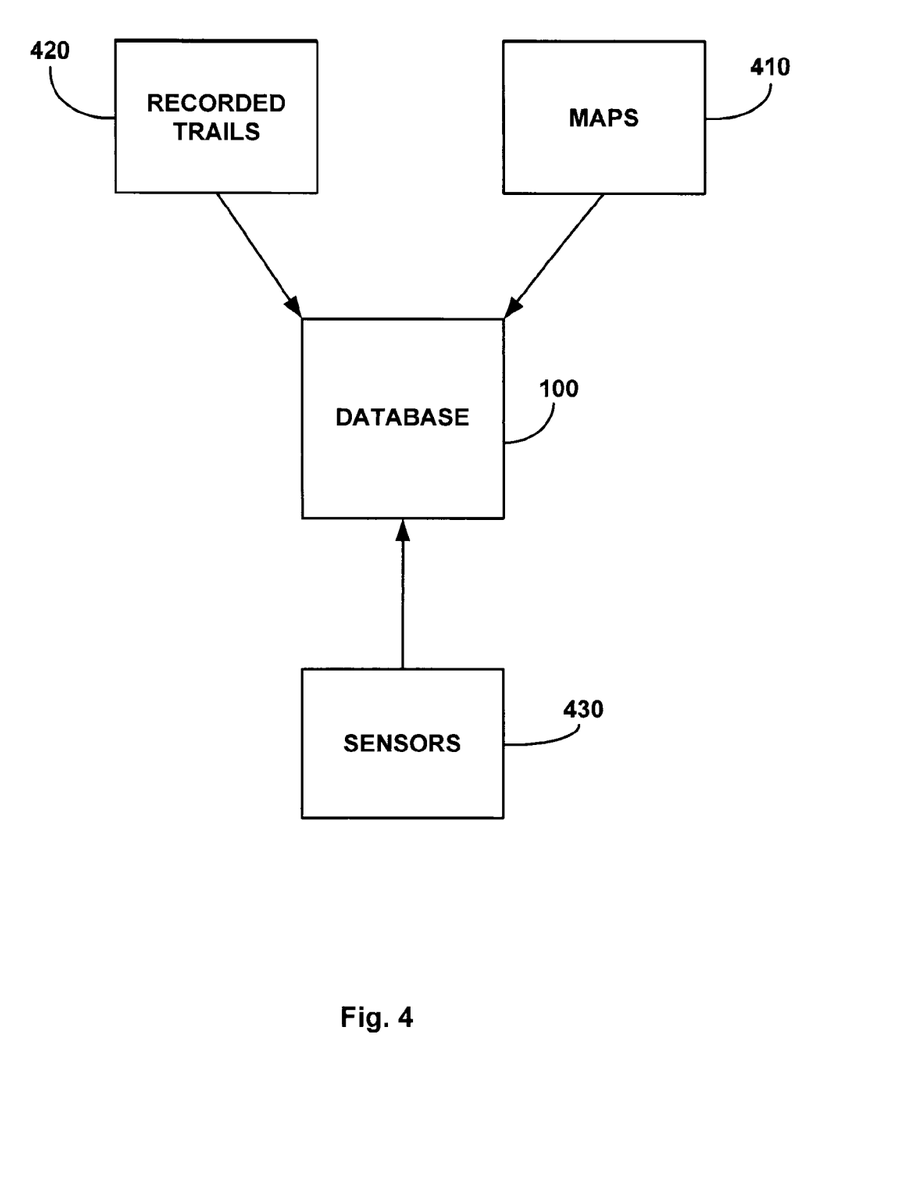
FIG. 4 is a schematic block diagram showing the various sources contributing to the creation and the on-going updating of the database.

FIG. 4 is a schematic block diagram showing the various sources contributing to the creation and the on-going updating of the database 100.

Maps 410—The basic database may be constructed using existing trails databases and/or user generated content or previously selected trails.

Existing trails databases may comprise various available Digital Elevation Models (DEM) such as the NASA DEM, or a database collected by GPS from users which are digital representations of elevations as measured at ground level. Such elevations are calculated using a variety of methods, including stereoscopy, digitized contour data, GPS data, radar signal interpretation or other methods for extracting elevation from a given position. CDEM (Canadian Digital Elevation Model) data sets for a region or a predefined area may be obtained using specific data extraction tools such as found on the web site geogratis.gc.ca.

Figure 5:
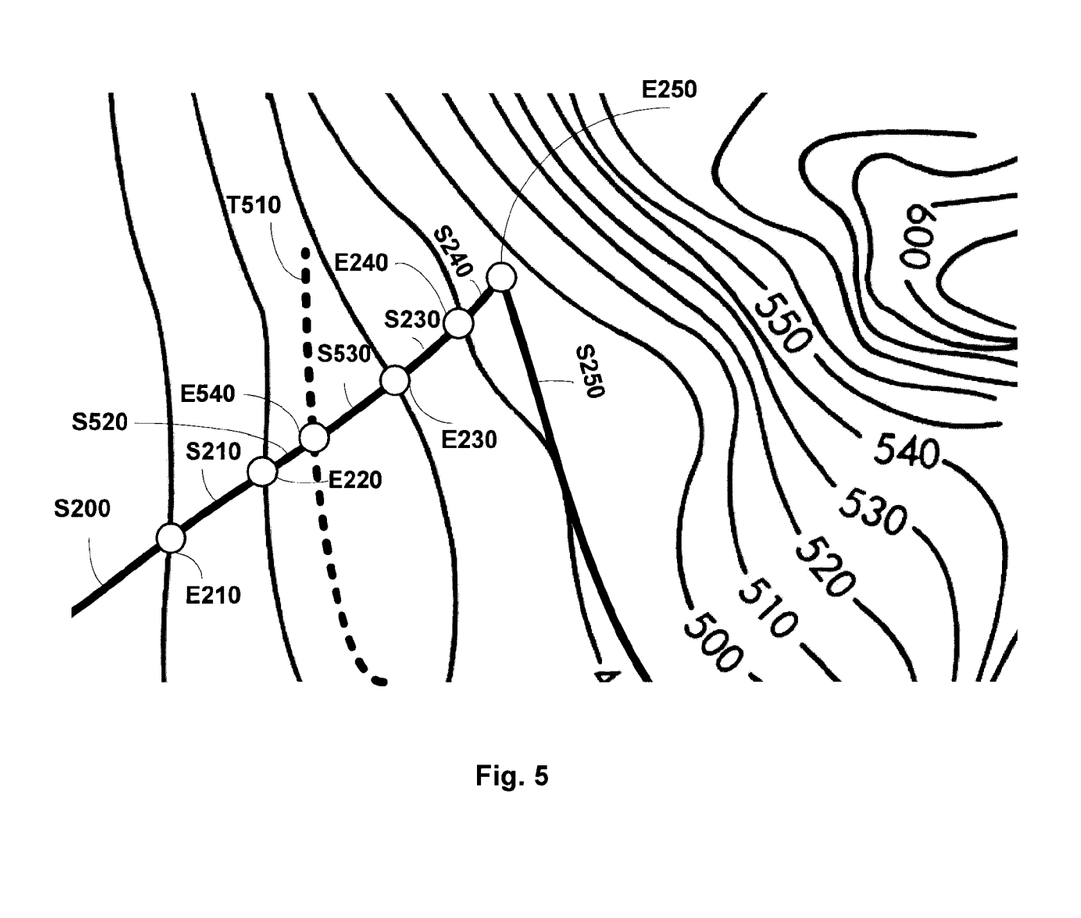
FIG. 5 shows an example of a segment being divided into two segments.
Figure 6A:
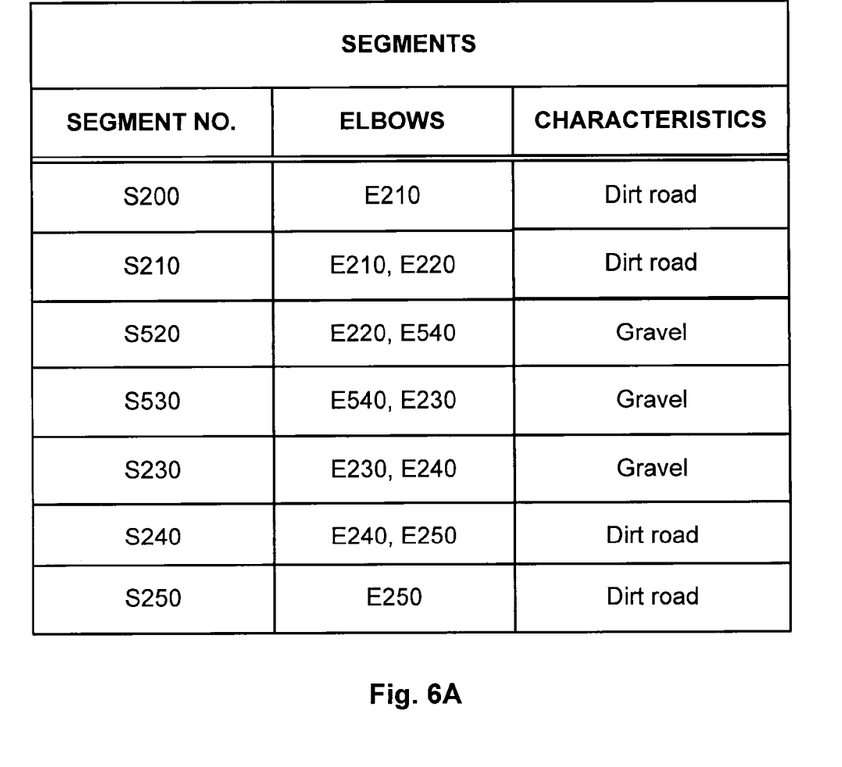
FIGS. 6A and 6B show exemplary database entries describing the segment division of FIG. 5.
Figure 6B:
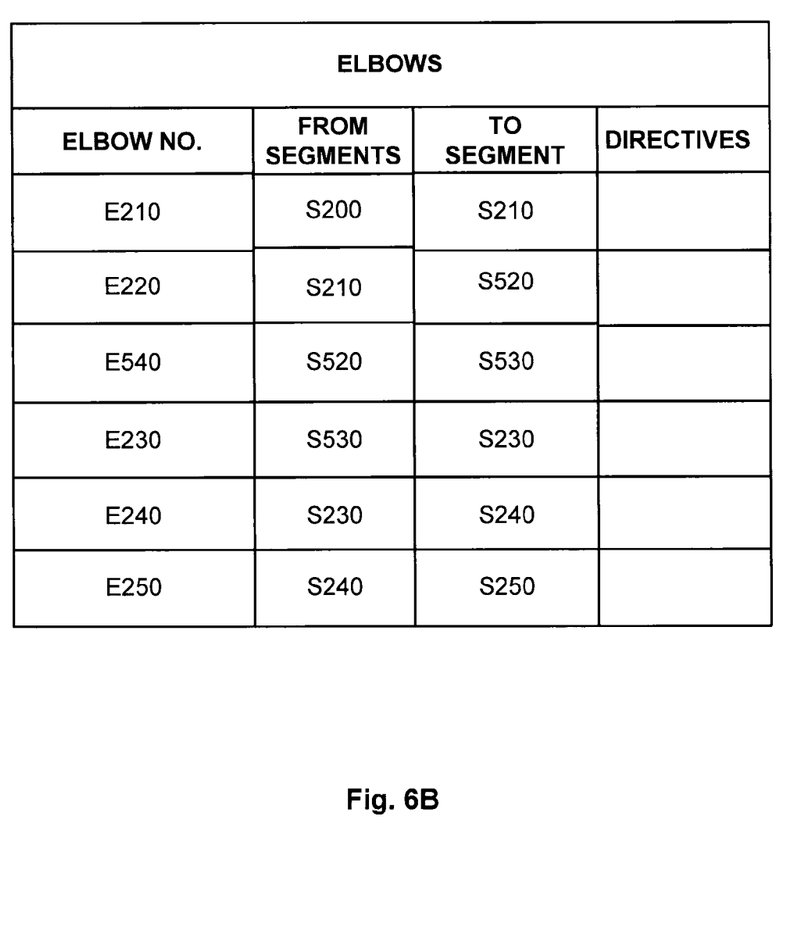

Recorded trails 420—Segments and elbows definitions may be continuously updated using recorded routes taken by travelers (e.g. by replaying captured location information). For example, if a recorded trail indicates traversing an existing segment, the segment may be divided into two segments connected by a new elbow. In the example of FIG. 5, using the partial map of FIG. 2 as a base, a new recorded trail T510 intersecting segment S220 causes the creation of a new elbow E540 which divides the previous segment S220 into two new segments S520 and S530. FIG. 6 shows the resulting updated database.

Sensors 430—Navigation directives for the various road segments may be continuously derived from various sensors carried or worn by the traveler. The sensors may comprise, for example:

Motion sensors—that measure acceleration forces and rotational forces along three axes. This category includes accelerometers, gravity sensors, gyroscopes, and rotational vector sensors.

Environmental sensors—that measure various environmental parameters, such as ambient air temperature and pressure, illumination, and humidity.

This category includes barometers, photometers, and thermometers.

Position sensors—that measure the physical position of a device. This category includes orientation sensors and magnetometers, Global Positioning System (GPS), European Geostationary Navigation Overlay Service (EGNOS), Global Navigation Satellite System (GLONASS), and others.

Wearable physiological monitoring sensors—that measure various physiological parameters of the wearer (traveler) such as, for example, electrocardiogram (ECG), heart rate, blood pressure, body temperature and others.

Cameras. Microphones.

The data aggregated from the various sensors is analyzed to determine terrain characteristics and levels of difficulty of trails. This computed data is then translated into directives stored in the elbows database in conjunction with the relevant segments.

The sensors data may also serve to update segments and elbows definition by identifying different characteristics in various parts of a segment, which may lead to automatically partitioning the segment into two or more segments according to the different terrain characteristics which require different directives.

Directives given to a traveler about to enter a route segment may indicate, for example, mounting slope, descending slope, sharp turn, rocky terrain, bridge over river, gravel, mud, hiking section etc.

The various indications will be translated into different directives depending on the type of traveling vehicle. For example, "rocky terrain" may be translated into "shift to 1st gear" for a 4-wheel drive vehicle and into "walk" for a bicycle rider or initiate an alarm message such as "careful: dangerous slope ahead".

The various directive are stored in the database along with references to the appropriate type of traveling vehicle.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof which would occur to persons skilled in the art upon reading the foregoing description. For example, the database of the present invention may be constructed and used also in conjunction with paved roads, typically in uncharted areas.

The invention claimed is:

1. A method of creating and continuously updating a database for mapping road terrain of various characteristics in three-dimensional terms, comprising:

defining a plurality of road segments, each road segment defined by two bounding elbows, using at least one of maps and recorded trails, wherein the defining of the plurality of road segments further comprise:

defining preliminary terrain characteristics for each road segment, wherein said preliminary terrain characteristics within each road segment are substantially homogenous and configured to be traversed using a single set of directives;

defining preliminary navigation directives for vehicles entering each road segment from each of the two bounding elbows based on the preliminary terrain characteristics for each road segment; and continuously updating the database using data aggregated from sensors carried by travelers, wherein the sensors are position sensors including at least one of: Global Positioning System (GPS), European Geostationary Navigation Overlay Service (EGNOS), and Global Navigation Satellite System (GLONASS).

2. The method of claim 1, wherein currently updating the database comprises updating segment definitions according to recorded trails intersecting existing road segments.

3. The method of claim 1, wherein currently updating the database comprises updating segment definitions according to sensors data indicating changes in terrain characteristics within existing road segments.

4. The method of claim 1, wherein the data aggregated from the sensors is analyzed to determine terrain characteristics and levels of difficulty of trails.

5. The method of claim 4, wherein the data aggregated from the sensors is translated into navigation directives stored in the database in conjunction with the relevant road segments.

6. The method of claim 1, wherein the data aggregated from the sensors is used to update road segments and elbows definitions by identifying different characteristics of various parts of a segment and partitioning the road segment into two or more road segments according to different terrain characteristics of each portion which require different navigation directives.

7. The method of claim 1, wherein the navigation directives are translated into appropriate directives depending on a type vehicle used.

8. The method of claim 1, wherein the sensors are further selected from the group consisting of: motion sensors, environmental sensors, wearable physiological monitoring sensors, and cameras and microphones.

9. The method of claim 8, wherein the motion sensors are selected from the group consisting of: accelerometers, gravity sensors, gyroscopes and rotational vector sensors.

10. The method of claim 8, wherein said environmental sensors are selected from the group consisting of: barometers, photometers and thermometers.

11. The method of claim 8, wherein the wearable physiological monitoring sensors are configured to measure physiological parameters selected from the group consisting of: electrocardiogram (ECG), heart rate, blood pressure and body temperature.

12. The method of claim 8, wherein at least one of the sensors is carried or worn by a traveler or installed in a vehicle.

* * * * *